US012257430B2

(12) United States Patent
Fried et al.

(10) Patent No.: US 12,257,430 B2
(45) Date of Patent: Mar. 25, 2025

(54) IMPLANTABLE MEDICAL LEAD SYSTEMS AND ADAPTERS (71) Applicant: MEDTRONIC, INC., Minneapolis, MN (US)

(72) Inventors: Andrew Fried, Minneapolis, MN (US); Steve Deininger, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 369 days.

(21) Appl. No.: 17/232,439

(22) Filed: Apr. 16, 2021

(65) Prior Publication Data
US 2021/0322765 A1 Oct. 21, 2021

Related U.S. Application Data
(60) Provisional application No. 63/010,728, filed on Apr. 16, 2020.

(51) Int. Cl.
*A61N 1/05* (2006.01)
*A61N 1/375* (2006.01)

(52) U.S. Cl.
CPC ......... *A61N 1/0551* (2013.01); *A61N 1/3752* (2013.01)

(58) Field of Classification Search
CPC .... A61N 1/0551; A61N 1/3752; H01R 24/58; H01R 2201/12; H01R 31/065
See application file for complete search history.

(56) References Cited

U.S. PATENT DOCUMENTS

| | | | |
|---|---|---|---|
| 9,002,471 B2 | 4/2015 | Stevenson et al. | |
| 11,679,256 B2* | 6/2023 | Sandgren | A61N 1/3752 607/117 |
| 2003/0149456 A1* | 8/2003 | Rottenberg | A61N 1/3752 607/37 |
| 2008/0140161 A1 | 6/2008 | Goetz et al. | |
| 2009/0024187 A1 | 1/2009 | Erickson et al. | |
| 2011/0270065 A1* | 11/2011 | Ternes | A61N 1/36114 607/32 |
| 2012/0130438 A1* | 5/2012 | Seeley | H01R 24/76 607/2 |
| 2012/0197356 A1 | 8/2012 | Wei et al. | |
| 2012/0232625 A1* | 9/2012 | Sage | A61N 1/0551 607/116 |
| 2014/0155951 A1 | 6/2014 | Doerr | |
| 2014/0200638 A1 | 7/2014 | Chow et al. | |

(Continued)

FOREIGN PATENT DOCUMENTS

EP 2198913 A1 6/2010

OTHER PUBLICATIONS

Analog Devices 16×16 Crosspoint Switch Array AD75019 brochure 2018.*

*Primary Examiner* — Mark W. Bockelman
(74) *Attorney, Agent, or Firm* — Shumaker & Sieffert, P.A.

(57) ABSTRACT

An implantable electrical stimulation medical system is disclosed. The system includes an implantable medical device having electrical circuitry configured to perform electrical stimulation, a nonstandard implantable medical lead, and an adapter matrix. The adapter matrix electrically interfaces with the electrical circuitry and the nonstandard implantable medical lead to provide electrical stimulation from the implantable medical device to the nonstandard implantable medical lead.

16 Claims, 3 Drawing Sheets

(56) References Cited

U.S. PATENT DOCUMENTS

| | | |
|---|---|---|
| 2015/0088227 A1 | 3/2015 | Shishilla et al. |
| 2015/0231396 A1 | 8/2015 | Burdick et al. |
| 2017/0281932 A1 | 10/2017 | Gerber |
| 2017/0333702 A1 | 11/2017 | Barner |
| 2019/0076645 A1* | 3/2019 | Bower ............... A61N 1/37211 |

* cited by examiner

IMPLANTABLE MEDICAL LEAD SYSTEMS AND ADAPTERS

CROSS-REFERENCE TO RELATED APPLICATION

This Non-Provisional Utility application claims benefit to U.S. Provisional Application No. 63/010,728, filed, Apr. 16, 2020, titled "IMPLANTABLE MEDICAL SYSTEMS AND ADAPTERS," the entirety of which incorporated herein by reference.

BACKGROUND

The present disclosure relates generally to a method and apparatus that allows for electrical stimulation of body tissue, such as sacral nerves. More specifically, this present disclosure relates to implantable electrical stimulation systems having an implantable medical device and an adapter that may configure a nonstandard implantable medical electrical lead having a stimulation electrode for the implantable medical device.

Implantable electrical stimulation systems are therapeutic in a variety of diseases and disorders. For example, spinal cord stimulation systems have been used as a therapeutic modality for treatment of chronic pain syndromes. Deep brain stimulation has been useful for treating refractory chronic pain syndromes, movement disorders, and epilepsy. Peripheral nerve stimulation has been used to treat chronic pain syndrome and pelvic floor disorders. Other applications are under investigation. Examples in this disclosure are presented with reference to peripheral nerve stimulation such as the stimulation of sacral nerves for illustration, but the methods and apparatus of this disclosure are not limited to sacral nerve stimulation or to peripheral nerve stimulation.

Pelvic floor disorders such as urinary incontinence, urinary urge/frequency, urinary retention, pelvic pain, bowel dysfunction (constipation, diarrhea), and sexual dysfunction are bodily functions influenced by the sacral nerves. Specifically, urinary incontinence is the involuntary control over the bladder that is exhibited in various patients. Incontinence is primarily treated through pharmaceuticals and surgery. Pharmaceuticals may not adequately resolve the issue and can cause unwanted side effects, and a number of the surgical procedures have a low success rate and are not reversible. Several other methods have been used to control bladder incontinence, for example, vesicostomy or an artificial sphincter implanted around the urethra. These solutions also have drawbacks. In addition, some disease states do not have adequate medical treatments.

The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles within the sacrum. The sacrum, generally, is a large, triangular bone situated at the lower part of the vertebral column, and at the upper and back part of the pelvic cavity. The spinal canal runs throughout the greater part of the sacrum. The sacrum is perforated by the anterior and posterior sacral foramina that the sacral nerves pass through.

Neurostimulation leads have been implanted on a temporary or permanent basis having a stimulation electrode (at least one stimulation electrode) positioned on and near the sacral nerves to provide partial control for bladder incontinence. Temporary sacral nerve stimulation is accomplished through implantation of a temporary neurostimulation lead extending through the skin and connected with a temporary external pulse generator. A permanent neurostimulator is implanted if stimulation is efficacious and it is possible to do so in the particular patient. Permanent implantation is accomplished by implanting a permanent neurostimulation lead, extending the proximal portion of the lead body subcutaneously, and connecting its proximal end with an implantable pulse generator, or IPG, implanted subcutaneously.

In one example, a lead bearing a distal stimulation electrode is percutaneously implanted through the dorsum and the sacral foramen of the sacral segment S3 for purposes of selectively stimulating the S3 sacral nerve. The lead is advanced through the lumen of a hollow spinal needle extended through the foramen, and the single distal tip electrode is positioned adjoining the selected sacral nerve. Stimulation energy is applied through the lead to the electrode to test the nerve response. The electrode is moved back and forth to locate the most efficacious location, and the lead is then secured by suturing the lead body to subcutaneous tissue posterior to the sacrum and attached to the output of a neurostimulator IPG. Despite the suture fixation, sacral nerve stimulation leads having a single discrete tip electrode can be dislodged from the most efficacious location due to stresses placed on the lead by an ambulatory patient. Surgical intervention can then be applied to reposition the electrode and affix the lead.

The current lead designs used for permanent implantation to provide sacral nerve stimulation through a foramen have several, e.g., four, of ring-shaped, stimulation electrodes spaced along a distal segment of the lead body adapted to be passed into or through the foramen along a selected sacral nerve. Each distal stimulation electrode is electrically coupled to the distal end of a lead conductor within the elongated lead body that extends proximally through the lead body. The proximal ends of the separately insulated lead conductors are each coupled to a ring-shaped connector element in a proximal connector element array along a proximal segment of the lead body that is adapted to be coupled with the implantable neurostimulation pulse generator, or neurostimulator IPG.

The electrode array is moved back and forth with respect to the sacral nerve while the response to stimulation pulses applied through one or more of the electrodes is determined. The IPG is programmed to deliver stimulation pulse energy to the electrode providing the optimal nerve response, and the selection of the electrodes can be changed if efficacy using a selected electrode fades over time due to dislodgement or other causes.

Electrical stimulation pulses generated by the neurostimulator IPG are applied to the sacral nerve through the selected one or more of the stimulation electrodes in either a unipolar or bipolar stimulation mode. In one unipolar stimulation mode, the stimulation pulses are delivered between a selected active one of the stimulation electrodes and the electrically conductive, exposed surface of the neurostimulator IPG housing or can that provides a remote, indifferent, or return electrode. In this case, efficacy of stimulation between each stimulation electrode and the neurostimulator IPG can electrode is tested, and the most efficacious combination is selected for use. In a further unipolar stimulation mode, two or more of the stimulation electrodes are electrically coupled together providing stimulation between the coupled together stimulation electrodes and the return electrode.

In a bipolar stimulation mode, one of the distal stimulation electrodes is selected as the indifferent or return electrode. Localized electrical stimulation of the sacral nerve is effected between the active stimulation electrode or electrodes and the indifferent stimulation electrode.

A issue associated with implantation of permanent and temporary neurostimulation leads involves placing and maintaining the discrete ring-shaped electrode or electrodes in casual contact, that is in location where slight contact of the electrode with the sacral nerve may occur or in close proximity to the sacral nerve to provide adequate stimulation of the sacral nerve, while allowing for some axial movement of the lead body.

In some examples, physicians spend a great deal of time with the patient under a general anesthetic placing the leads due to making an incision exposing the foramen and due to the difficulty in optimally positioning the small size stimulation electrodes relative to the sacral nerve. In other examples, an incision is made in the skin and a needle and guide are placed into the foramen. The patient is exposed to dangers associated with extended periods of time under a general anesthetic in order to get adequate placement. Movement of the lead, whether over time from suture release or during implantation during suture sleeve installation, is to be avoided. Also, unintended movement of any object positioned proximate a nerve may cause unintended nerve damage. Moreover, reliable stimulation of a nerve entails consistent nerve response to the electrical stimulation that, in turn, entails consistent presence of the stimulation electrode proximate the sacral nerve. But too close or too tight a contact of the electrode with the sacral nerve can also cause inflammation or injury to the nerve diminishing efficacy and possibly causing patient discomfort.

Once the optimal electrode position is attained, the lead body is fixed to retard lead migration and dislodgement of the electrodes from the optimal position employing sutures or sacral lead fixation mechanisms.

Once fixation is completed, the proximal lead body is typically bent at about 90° and tunneled subcutaneously to a remote site where its proximal connector elements are coupled to the neurostimulator IPG which is then implanted at the remote site. In this process some axial and lateral dislodgement of the stimulation electrodes can also occur.

It is generally desirable to minimize surgical trauma to the patient through surgical exposure of the tissue and sacrum. It is preferred to employ a minimally invasive, percutaneous approach in a path extending from the skin to the foramen that the neurostimulation lead is extended through.

One such percutaneous approach for implantation includes a temporary neurostimulation lead that extends through the patient's skin and is attached to an external pulse generator. Typically, the external pulse generator and exposed portion of the lead body are taped to the skin to inhibit axial movement of the lead body. When a stimulation time period ends, the lead is removed through the skin by application of traction to the exposed lead body, and the incision is closed. The neurostimulation lead bodies are formed with surface treatment or roughening in a portion proximal to the neurostimulation electrode expected to extend from the foramen to the patient's skin that is intended to increase the resistance to unintended axial dislodgement of the lead body to stabilize the electrode. A length of the lead body is formed with indentations or spiral ridges or treated to have a macroscopic roughening.

A number of configurations of implantable medical electrical leads other than neurostimulation leads employ fixation mechanisms to maintain a stimulation electrode in relation to a body organ or tissue. Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known. Such tined leads typically employ three or four tines that extend outwardly and proximally from a band proximal to a distal tip pace/sense electrode and that catch in natural trabecular interstices when the distal tip electrode is advanced into the atrial appendage or the ventricular apex. Certain spinal cord stimulation leads have been proposed employing tines and/or vanes as stand-offs to urge the stimulation electrode in the epidural space toward the spinal cord and to stabilize the stimulation electrode in the epidural space, In an example directed to atrial tined leads, longitudinally extending rows of elongated tines were provided within a 270° arc extending away from a distal tip electrode canted in the remaining 90° section. The multiple rows of tines were intended to lodge in the trabecular interstices and force the canted tip against the atrial endocardial wall. However, it was found in practice that the canted tip is unnecessary and that only three, much shorter, tines in the 270° arc or four tines spaced apart by 90° in a common circumference like a ventricular tined lead, are sufficient. The rows of tines are necessarily closely spaced because of the small area of trabeculae in the right atrium, and more proximal tines simply typically do not engage anything and make it difficult to lodge any of the tines in the interstitial spaces.

At times, components of the implantable electrical stimulation system may be replaced. For example, the neurostimulator IPG may be replaced because of a component failure or because another model of neurostimulator IPG is to be used for therapy. In such circumstances, given the difficulty of placing and positioning the implantable medical lead, a clinician may prefer to leave in place the lead. Also, for example, the implantable medical lead may be replaced because of a component failure or because a medical lead with a particular fixation mechanism is preferred. In such circumstances, the clinician may prefer to continue therapy with the particular neurostimulator IPG. Generally, neurostimulator IPGs are not configured to universally work with implantable medical leads based on such factors as varying sizes and configurations of interface elements. In some circumstances, a desire to replace one component in an implantable electrical stimulation system may cause replacement of the entire electrical stimulation system in order for the replaced component or components to work in a system.

SUMMARY

To summarize the current techniques of deploying implantable electrical stimulation systems include coupling a neurostimulator IPG to a corresponding standard implantable medical lead. In many examples, the corresponding standard implantable medical lead is directly received within the neurostimulator IPG. In some examples a medical lead having electrodes configured to interface with tissue is coupled to an intermediate elongate conductor, such as a lead extender, which is then directly coupled to the neurostimulator IPG. In these examples, the lead extender is a standard lead extender, and for the purposes of this disclosure, can function as a standard implantable medical lead. A nonstandard implantable medical lead, however, is not configured to be directly coupled to the neurostimulator IPG. In the case of desire to use the neurostimulator IPG with a nonstandard implantable medical lead in the implantable electrical stimulation system, an adapter matrix can be included in the system to operably couple the neurostimulator IPG with the nonstandard implantable medical lead as set forth in this disclosure.

The adapter matrix provides a bridge to connect neurostimulator IPG with a nonstandard implantable medical lead to form an implantable electrical stimulation system. The adapter matrix is electrically coupled to the stimulation circuitry in the neurostimulator IPG, and the nonstandard implantable medical is electrically coupled, such as received in a tissue-facing input, to the adapter matrix. Electrical connections in the adapter matrix are provided to make electrical communication between the stimulation circuitry in the neurostimulator IPG and the nonstandard implantable medical lead in the implantable electrical stimulation system.

In one example, a standard lead is coupled to the neurostimulator IPG. For instance, the neurostimulator IPG receives a proximal end of the standard implantable medical lead, which can include a connector matrix. The distal end of the standard implantable medical lead, which can include an electrode array, is coupled to the adapter matrix. The adapter matrix can receive the proximal end of a nonstandard implantable medical lead, which can include a nonstandard connector matrix. The distal end of the nonstandard implantable medical lead, which can include an electrode array, is positioned to interface with tissue such as proximate a sacral nerve, to provide a stimulation signal to the tissue generated by the neurostimulator IPG and can in some examples, provide electrical signals received at an electrode to the neurostimulator IPG.

The adapter matrix includes a neurostimulator IPG-facing input having a first set of electrical connections that can interface with conductors on a distal end of a cable, in which the cable includes a proximal end to be received in the neurostimulator IPG. In one example, the cable is a standard implantable medical lead and the distal end of the standard implantable medical lead includes an electrode array. In this example, the first set of electrical connections include electrical connections configured to interface with the electrode array in the standard implantable medical lead. In another example, neurostimulator IPG-facing input includes the first set of electrical connectors adapted to receive a specialized cable having a distal end with specialized conductors. The specialized conductors may be adapted to fit within the adapter matrix and not designed to interface with tissue. For instance, the specialized cable may have a shorter length than a suitable implantable medical lead or a distal end having electrical conductors not configured as electrodes but configured to be especially received in the neurostimulator IPG-facing input of the adapter matrix. The proximal end, however, may include a connector array similar to a lead designed to interface with tissue and, in particular, be received within the neurostimulator IPG.

The adapter matrix also includes a tissue-facing input having a second set of electrical connections that can interface with conductors on a proximal end of a nonstandard implantable medical lead. In one example, the second set of conductors are configured at a relatively dense spacing as microprobes such that one or more active conductors of the second set of conductors may electrically interface with a conductor of the conductor array on the proximal end of the nonstandard implantable medical lead received within the tissue-facing input of the adapter matrix. Furthermore, one or more inactive conductors of the second set of conductors may contact insulated portions of the proximal end of the nonstandard implantable medical lead, such as in between the connectors of the connector array, received within the tissue-facing input of the adapter matrix. In one example, the tissue-facing input can be configured to receive a number of different designs of nonstandard implantable medical leads as well as a standard implantable medical lead. For instance, the tissue facing input can be configured to receive a number of different diameters of the nonstandard implantable medical lead and include a coupling mechanism to connect the proximal end of the nonstandard implantable medical lead to the adapter matrix and secure the active conductors of the second set of conductors against the respective connectors of the connector matrix.

The adapter matrix further includes a switch matrix to selectively electrically couple the first set of conductors of the adapter matrix to the second set of conductors. The switch matrix, in one example, is programmable such that the electrical connections of the cable received within the neurostimulator IPG-facing input can selectively correspond with connectors of the connector matrix of the nonstandard implantable medical lead. Electronics for the switch matrix can be included within an adapter matrix case, or the adapter matrix may be included within neurostimulator IPG.

In some examples, the adapter matrix is operated with a power source. The power source may be a primary cell or rechargeable power source. In another example, the adapter matrix is configured to receive power from the neurostimulator IPG. In some examples, the adapter matrix includes communication circuitry or a physical interface.

DETAILED DESCRIPTION

Aspects of the present disclosure provide for implantable medical devices, methods of manufacturing such implantable medical devices, and implantable medical device systems including such implantable medical devices.

Figure 1:
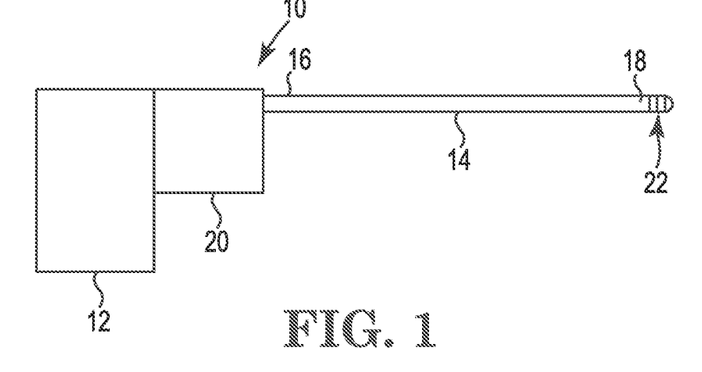
FIG. 1 is a schematic view illustrating an example implantable medical system.

FIG. 1 illustrates an implantable medical device system 10. System 10 includes an implantable medical device (IMD) 12, an implantable medical lead 14, and an implantable adapter matrix 20 that may interface between the implantable medical device 12 and the implantable medical lead 14. In general terms, the implantable medical device 12 may be of various types, such as a device for producing electrical stimulation or for sensing physiological signals for various medical applications such as neurological or cardiac therapy. The implantable medical lead 14 includes a proximal end 16 of a lead body in which a series of electrical contacts are located. Each electrical contact has a corresponding conductor within the lead body that extends to a distal end 18 in which a series of electrodes 22 are present. During use, the proximal end 16 is inserted into the adapter matrix 20, and the adapter matrix 20 may include or receive conductors that are adapted to be coupled into the implantable medical device 12, establishing electrical interface between the electrical contacts of the implantable medical lead 14 and electrical connectors carried by the implantable medical device 12 via the adapter matrix 20. Stimulation signals generated by the implantable medical device 12 are delivered to the distal end 18 of the implantable medical lead 14 via electrodes 22 and to targeted tissue and/or signals sensed by the distal end of the implantable medical lead 14 at the targeted tissue are delivered to the implantable medical device 12 via the adapter matrix 20. The systems of the present disclosure can optionally include one or more additional components, such as one or more handset programmers configured and programmed to wirelessly interface with the implantable medical device 12 or the adapter matrix 20.

In one example, the implantable medical device 12 may have electrical connectors that are configured to receive the proximal end of a first implantable medical lead, or standard implantable medical lead. The clinician, however, may prefer to provide electrical stimulation to tissue with a second implantable medical lead, or a non-standard implantable medical lead, such as implantable medical lead 14. In the example, the electrical connectors of the implantable medical device 12 are not configured to receive or interface with the non-standard implantable medical lead 14. The adapter matrix 20 can include an input conductor configured to be received in the electrical connectors of the implantable medical device 12. The adapter 20 can include an output configured to receive the proximal end of the non-standard implantable medical lead 14. The adapter matrix 20 provides electrical connections to allow electrical signals to pass between the implantable medical device 12 and the distal end electrodes of the non-standard medical lead 14.

In some examples, the system 10 and the implantable medical device 12 is configured to be useful or appropriate for providing stimulation therapy to a patient, and in particular sacral neuromodulation. In some examples, the system 10 can be described as an implantable programmable neuromodulation system that delivers electrical stimulation to the sacral nerve. Sacral neuromodulation therapy provided by the system 10 can be indicated for the management of the chronic intractable functional disorders of the pelvis and lower urinary or intestinal tract including overactive bladder, fecal incontinence, and nonobstructive urinary retention.

Sacral neuromodulation creates an electrical field near the sacral nerve to modulate the neural activity that influences the behavior of the pelvic floor, lower urinary tract, urinary and anal sphincters, and colon. The system 10 is configured to use current controlled stimulation to generate an electric field to modulate the sacral nerve. Electrical stimulation is delivered using metal electrodes provided with the implantable medical lead 14, which carry current in the form of electrons, to biological tissue, which carries current in the form of ions. An interface between the electrode and the tissue includes non-linear impedance that can be a function of the voltage across that interface. During current-controlled stimulation, an amount of current is regulated. The voltage is changed according to the actual value of impedance, such that changes in impedance will not affect the total amount of current delivered to the tissue. Current controlled waveforms can ensure that the electric field in the tissue is independent of electrode polarization or the voltage drop across the electrode-electrolyte interface. Alternatively, the systems of the present disclosure can be configured or programmed to use voltage-controlled stimulation.

The adapter matrix 20 can be surgically installed, or placed, in the same tissue pocket of a patient as the implantable medical device 12 or in a separate tissue pocket. In some embodiments, the adapter matrix may be rigidly attached to the implantable medical device. In other embodiments, the interface between the adapter matrix 20 and the implanted medical device 12 may be of sufficient length to place the adapter matrix in a separate pocket. For example, if the implanted medical device 12 is rechargeable and the adapter matrix has a metallic enclosure, it may be beneficial to have the adapter matrix 20 at least 10 cm away so that inductive energy to charge the neurostimulator does not induce eddy currents in the adapter matrix. If the adapter matrix 20 is placed in the same tissue pocket as the implantable medical device 12, the adapter matrix 20 can include its own power source and either communicate via the implantable medical device 12 or the adapter matrix 20 can include its own communication capability and communicate independently of the implantable medical device 12. Also, the adapter matrix 20 can include its own physical user interface an implemented without a power supply in the adapter matrix 20. In another example of an adapter matrix 20 configured to be placed in the same pocket as the implantable medical device 12, the adapter matrix 20 can be coupled to and receive power from the implantable medical device power source and either communicate via the implantable medical device 12 or the adapter matrix 20 can include its own communication capability and communicate independently of the implantable medical device 12. If the adapter matrix 20 is configured to be placed in a separate tissue pocket from the implantable medical device 12, the adapter matrix 20 can be coupled to the implantable medical device 12 via an extension lead, such as a lead a few inches long, or a standard implantable medical lead.

Figure 2:
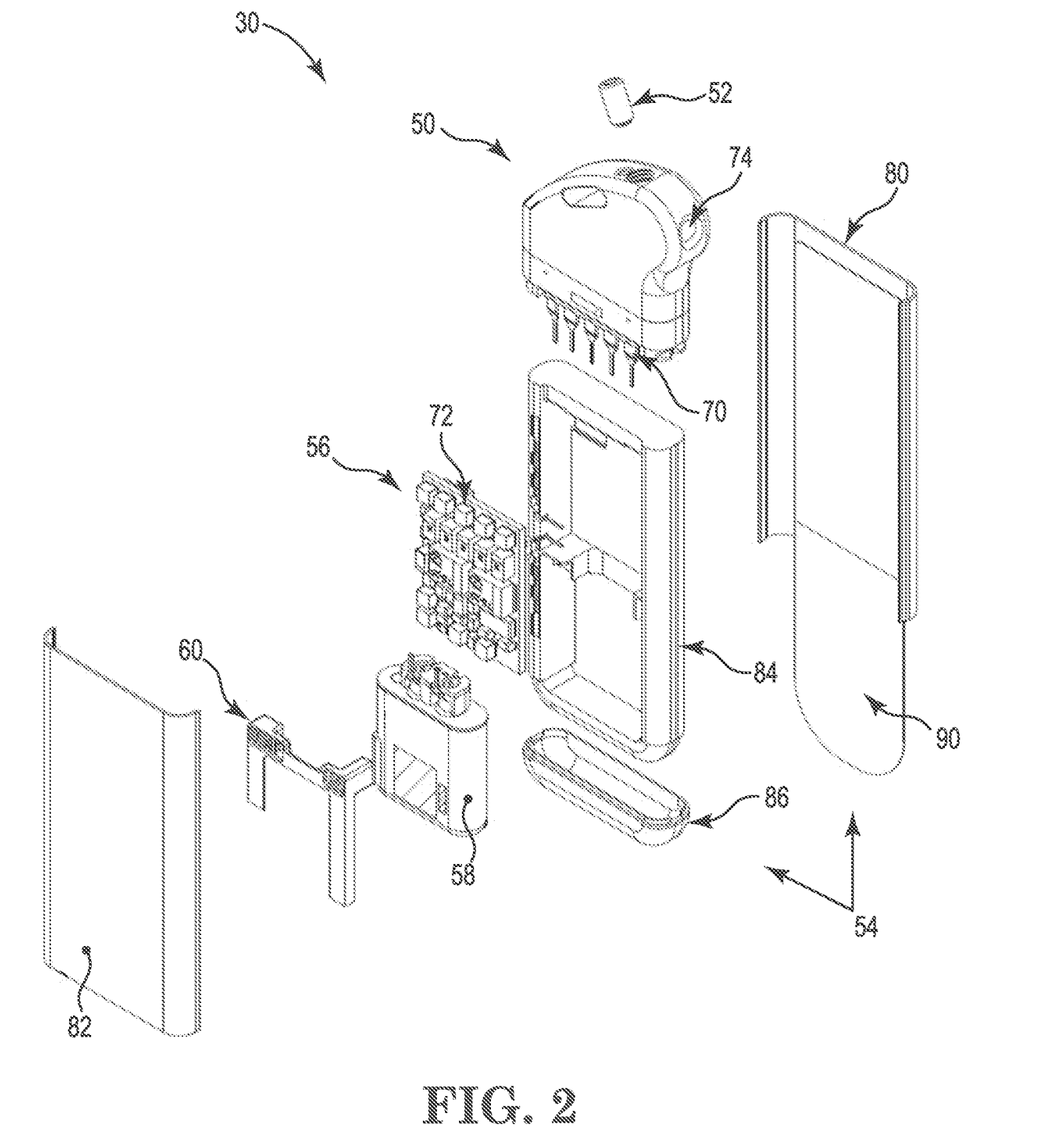
FIG. 2 is an exploded perspective view illustrating an example implantable medical device useful with the implantable medical system of FIG. 1.

FIG. 2 illustrates an example of the implantable medical device 30 appropriate, for example, for generating the sacral neuromodulation therapy stimulation signals, which may be an example of implantable medical device 12 in system 10. The implantable medical device 30 can be configured to provide a small form factor, e.g., a volume on the order of approximately 3 cubic centimeters in some non-limiting embodiments, while generating desired stimulation signals over an extended lifetime. The implantable medical device 30 can serve as the power source of the sacral neuromodulation therapy described above in some embodiments. The smaller form factor or size as compared to conventional stimulation-type implantable medical devices can allow for a smaller implant location incision and smaller subcutaneous pocket, which may result in a more discreet implant. In some embodiments, the implantable medical device 30 incorporates various features described below that facilitate the small form factor size while providing desired performance attributes, such as remotely programmable stimulation signals or electrical pulses at therapy levels of interest, magnetic resonance imaging (MM) compatibility, and remote charging.

In some examples, the implantable medical device 30 includes or defines a connector enclosure assembly 50, a set screw 52, a main enclosure assembly or can 54, electrical circuitry 56, a battery 58, and an optional desiccant assembly 60. Details on the various components are provided below. In general terms, the electrical circuitry 56, the battery 58 and the desiccant assembly 60 are maintained within the can 54. The battery 58 is electrically coupled to the electrical circuitry 56. The connector enclosure assembly 50 is assembled to the can 54, and includes one or more conductor fingers 70 that are electrically connected to individual circuitry components, and in particular contact pads 72, of the electrical circuitry 56. With this construction, electrical signals generated by the electrical circuitry 56 are delivered to the connector enclosure assembly 50 via the conductor fingers 70. The connector enclosure assembly 50 further forms or defines an entryway 74 sized to receive a proximal end of an implantable medical lead, such as a standard implantable medical lead. Electrical connectors provided with the connector enclosure assembly 50 interface with the electrical contacts on the standard implantable medical lead and are electrically connected to respective ones of the conductor fingers 70, thereby connecting the electrical circuitry 56 with the standard implantable medical lead. The set screw 52 provides an electrical ground between the standard implantable medical lead as inserted into the entryway 72 and the can 54.

The can 54 can assume various forms appropriate for maintaining the electrical circuitry 56 and the battery 58, as well as for assembly with the connector enclosure assembly 50. In some embodiments, the can 54 includes opposing shield bodies 80, 82, an insulator cup 84 and an end cap 86. The shield bodies 80, 82 can be formed of a surgically safe, robust material, e.g., titanium, such as a titanium alloy 6A1-4V ELI alloy per ASTM F136, and collectively generate a sleeve, e.g., the shield bodies 80, 82 can be secured to one another by, for example, laser seam welding applied to the interfacing edges. The sleeve, in turn, defines an open volume sized and shaped to receive the insulator cup 84. To facilitate final construction, a pressure sensitive adhesive liner 90 can be provided with the first shield body 80 that is removed prior to assembly to the insulator cup 84. A bottom opening to the sleeve collectively defined by the shield bodies 80, 82 is closed by the end cap 86. The end cap 86 and the connector enclosure assembly 50 can be assembled (e.g., welded) to the shield bodies 80, 82 to provide a hermetically sealed case.

The insulator cup 84 serves as a chassis, sized and shaped to fit snugly between the shield bodies 80, 82. The insulator cup 84 spatially secures the electrical circuitry 56 and the battery 58 via appropriately sized and shaped cavities. The insulator cup 84 can be formed of an electrically non-conductive or insulative material, such as a polymer.

The electrical circuitry 56 can include various electrical components and connections appropriate for providing, in some non-limiting embodiments, a pulse generator for therapy stimulation, e.g., a constant current stimulation engine, sensing circuitry for measuring physiological parameters, telemetry for communication with external devices (e.g., inductive telemetry at 175 KHz), memory, and a recharge circuit in some non-limiting embodiments. For example, the electrical circuitry 56 can deliver stimulation signals to the contact pads 72, and can process or act upon sensed signals received at the contact pads 72. The electrical circuitry 56 optionally provides various stimulation signal parameters, for example current controlled amplitude with a resolution of 0.1 mA steps, an upper limit of 12.5 mA, and a lower limit of 0.0 mA; a rate of 3-130 kHz; pulse width increments of 10 μs steps with a maximum of 450 μs and a minimum of 20 μs.

The battery 58 can assume various forms appropriate for generating desired stimulation signals, and in some embodiments is a rechargeable battery. For example, the battery 58 can incorporate lithium ion (Li+) chemistry, although other battery constructions or power storage device are also acceptable.

The desiccant assembly 60 is sized and shaped for mounting within the can 54, and provides or carries an appropriate desiccant material to promote a dry environment within the can 54.

The connector enclosure assembly 50 can be mounted to the can 54 in a hermetically sealed fashion. The conductor fingers 70 and the ground conductor 124 are arranged to extend to a corresponding one of the contact pads 72, and are welded, e.g., pressure gas welding. The desiccant assembly 60 can be placed into the can 54 following the welding process, or otherwise delayed until a remaining step is to add the second shield body 82. In this manner, the desiccant is exposed to the ambient conditions for only a short time prior to the interior of the can 54 being isolated from the exterior. This can preserve the effectiveness of the desiccant.

In one example, the adapter matrix 20 can be included in the electrical circuitry 56 and disposed within the can 54. In such an example, the adapter matrix 20 is configured so that the implantable medical device 30 can interface directly with the nonstandard implantable medical lead 14. The adapter matrix 20, in this example, can be powered from the battery 58 or other power source for the electrical circuitry 56. The adapter matrix can also apply communication circuitry of the electrical circuitry 56. In one particular example, the adapter matrix 20 can be operably coupled to conductor fingers, and configured to receive a non-standard implantable medical lead within the entryway 74.

Figure 3:
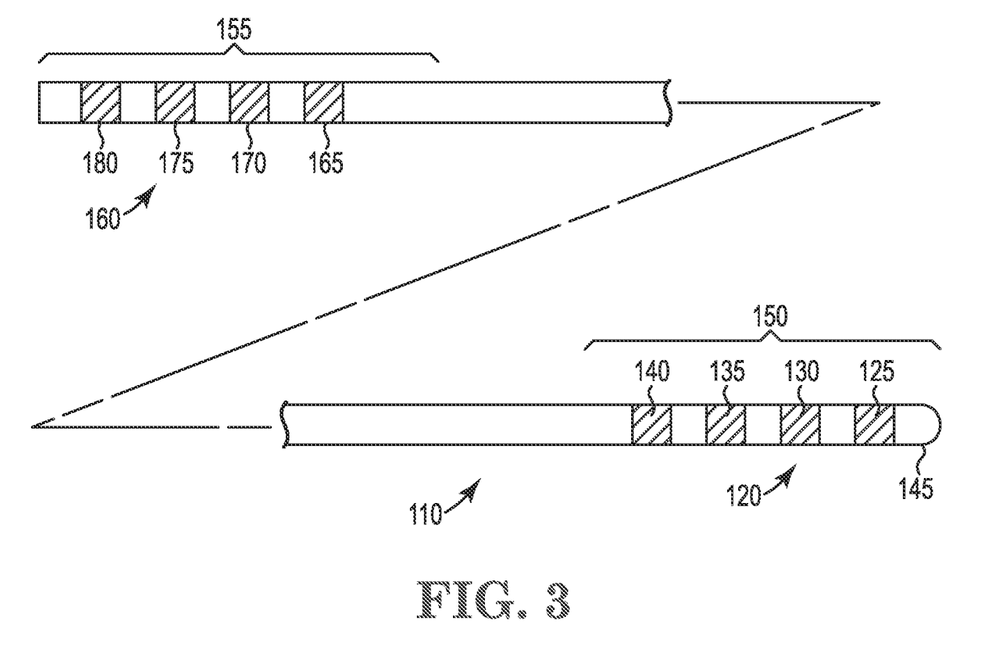
FIG. 3 is a plan view illustrating an example implantable medical lead useful with the implantable medical system of FIG. 1.

FIG. 3 illustrates an implantable medical lead 110, which can be an example of implantable medical lead 14. The implantable medical lead 110, in one example may be applied to provide non-direct contact stimulation of the sacral nerves. The implantable medical lead 110 comprises a lead body 115 and a ring-shaped electrode, such as four ring-shaped electrode 125, 130, 135, and 140 in an electrode array 120 extending proximally from the lead distal end 145. An electrode array 120 can include one or more electrodes. For example, an implantable medical lead could include an electrode array with a single electrode disposed on the distal end of the lead body. Other configurations are contemplated. An outer diameter of the lead body 115 can be in the range of about 0.5 mm to about 2 mm, and the lead 110 can be of a suitable length, such as about 28.0 cm long. The electrode array 120 with four ring electrodes can extends proximally longitudinally for a length of about 25.0 mm from the distal end 145. In one example, the electrodes 125, 130, 135 and 140 are made of a solid surface, bio-compatible material such as a tube formed of platinum, platinum-iridium alloy, or stainless steel, of about 3.0 mm in length that does not degrade when electrical stimulation is delivered through it separated by shorter insulator bands.

Each stimulation electrode 125, 130, 135, and 140 is electrically coupled to the distal end of a coiled wire lead conductor within the elongated lead body 115 that extends proximally through a distal portion 150 and through a proximal portion 155 of the lead body 115. The proximal ends of the separately insulated lead conductors are each coupled to respective ring-shaped connector elements 165, 170, 175, and 180 in a proximal connector element array 160 along the proximal portion 155 of the lead body 115 adjacent the lead proximal end 185. The conductor wires can be formed of an MP35N alloy and are insulated from one another within an insulating polymer sheath such as polyurethane, fluoropolymer, or silicone rubber. An example diameter of the lead body 115 is 1.3 mm but smaller diameters are also contemplated. The lead conductor wires can be separately insulated by an insulation coating and are wound in a quadra-filar manner having a common winding diameter within the outer sheath. The coil formed by the coiled wire conductors defines a lead body lumen of the lead body 115. In some examples, a further inner tubular sheath could be interposed within the aligned wire coils to provide the lead body lumen.

The implantable medical lead 110 can include a number of configurations including dimensions of diameter and the connector element array 160 or number of electrodes in the electrode array 120. For example, an implantable medical lead that includes a proximal end size, size and spacing of connector elements, and number of electrodes that are configured to be received within the implantable medical device 30 without an adapter matrix and configured to work with the implantable medical device 30 can be considered a standard implantable medical lead. Alternatively, an implantable medical lead that does not include a proximal end size, size or spacing of connector elements, or number of electrodes that are configured to be received within the implantable medical device 30 or configured to work with the implantable medical device 30 can be considered a non-standard implantable medical lead.

Figure 4:
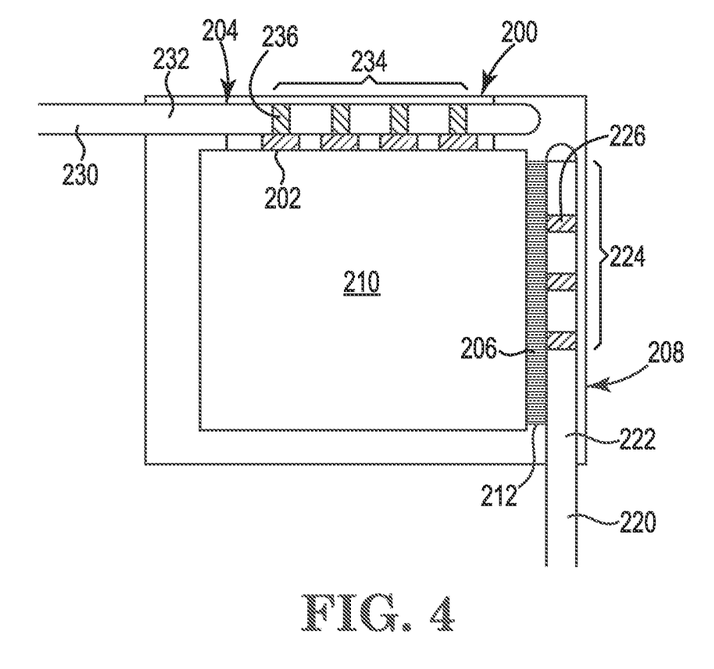
FIG. 4 is a schematic view illustrating an example adapter matrix of the implantable medical system of FIG. 1.

FIG. 4 illustrates an adapter matrix 200, which can be an example of adapter matrix 20. The adapter matrix includes a first set of electrical connections 202 disposed in a neurostimulator IPG-facing input 204, a second set of electrical connections 206 disposed in a tissue-facing input 208, and a switch matrix 210 to selectively electrically couple a connector of the first set of electrical connection 202 to a connector of the second set of electrical connections 206. For example, the switch matrix 210 can be implemented to selectively couple one of the electrical connections of the first set of electrical connections 202 to one or more electrical connections of the second set of electrical connections 206. In this example, the switch matrix 210 is programmable to selectively couple one of the electrical connections of the first set of electrical connections 202 to one or more electrical connections of the second set of electrical connections 206.

In one example of the adapter matrix 200, the neurostimulator IPG-facing input 204 is included in the implantable medical device 30 and first set of electrical connections 202 are electrically connected to stimulation circuits of the electrical circuitry 56. The tissue-facing input 208 is operably coupled to receive a nonstandard implantable medical lead, such as nonstandard implantable medical lead 220 having a proximal end 222 including a connector array 224 with connectors 226, in which the second set of electrical connections 206 are coupled to the connector array 224.

In an example in which the adapter matrix 200 in the implantable electrical stimulation system is not included with the implantable medical device 30, the adapter matrix 200 can be electrically coupled to the implantable medical device 30 with an extension lead 230. The extension lead 230 can include a distal end 232 having a connector array 234 including electrical connectors 236. For example, the extension lead 230 can include a standard electrical lead and the connector array 234 is an electrode array. The neurostimulator IPG-facing input 204 is configured to receive the distal end 232, and the first set of electrical connections 202 are sized and spaced to interface with the electrical connectors 236. In this example, the extension lead can include a proximal end (not shown) that includes conductors to interface with the electrical circuitry, such as via the conductor figures 70 within entryway 74. In the example illustrated the neurostimulator IPG-facing input 204 of the adapter matrix 200 includes a x-to-y correspondence between the connectors 236 of connector array 234 on the lead 230 and the first set of electrical connectors 202. For example, each one of the connectors 236 of the lead 230 interfaces with, such as mechanically and electrically connects with, one of the connectors of the first set of electrical connectors 202 as illustrated. In one example, each connector of the first set of electrical connectors is sized to effectively conduct a signal via a connector 236 on the lead 230, and the connectors of the first set of electrical connectors are spaced apart to as to interface with the connectors 236 of the lead, or spaced-apart at a distance that is generally same as the distance of spacing of the connectors 236 of the lead 230, as illustrated. Other examples are contemplated such as each one of the connectors 236 of the lead 230 can interface with a selected number of more than one of the connectors of the first set of electrical connectors 202, such as a one-to-two correspondence or a one-to-three correspondence.

The tissue-facing input 208 is operably coupled to receive the nonstandard implantable medical lead 220 in which the second set of electrical connections 206 are coupled to the connector array 224. The nonstandard implantable medical lead 220 can be secured to the adapter matrix 200 such that the connectors 226 do not move with respect to the second set of electrical connections 206. For example, the nonstandard implantable medical lead 220 can be secured to the adapter matrix 200 via a medical adhesive or a set screw. In one example, the adapter matrix 200 can include a transparent window over the tissue-facing input 208 so that a clinician can view the second set of electrical connections 206 and determine which of the second set of electrical connections 206 are in contact with which of the connectors 226 of the connector array 224.

The switch matrix 210 can be specifically constructed for the adapter matrix 200 or a commercially available integrated circuit. For example, the switch matrix 210 can include an integrated circuit available under the trade designation AD75019 16×16 Crosspoint Switch Array from Analog Devices, Inc., of Norwood, Massachusetts. For instance, a number of such integrated circuits can be coupled together to provide a selected number of second set of electrical connections 206 (such as 16, 32, 64, 128 . . . electrical connections 206 in the tissue-facing input). The integrated circuit can receive power and serial communication for operation, and the adapter matrix 200 can include electrical circuitry such as a microprocessor to provide operation such a switch function management.

Figure 5:
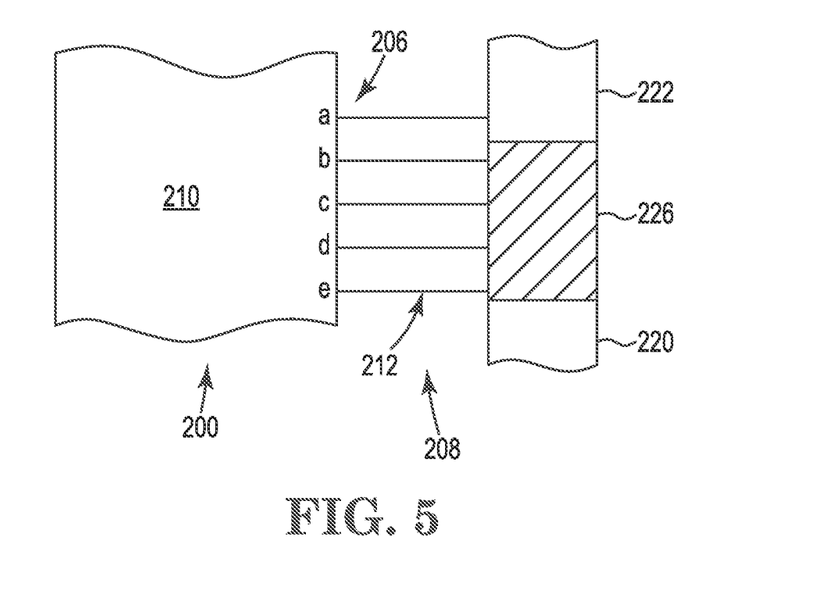
FIG. 5 is a schematic view illustrating a portion of the example adapter matrix of FIG. 4.

FIG. 5 illustrates a close-up view of the tissue-facing input 208 of adapter matrix 200 indicating the second set of electrical connections 206 are comprised of microprobes 212 that extend from the switch matrix 210 in microprobe array. In one example, the microprobes 212 can include electrically conductive, needle-like projections from the switch matrix 210. In one example, the tissue-facing input 208 may include 64 or 128 microprobes in the microprobe array, and the microprobes in the microprobe array are of a number greater than and spaced together more closely than the electrical connectors 226 in the connector array 224. In one example, the microprobes 212 in the microprobe array are of a number greater than and spaced together more closely than the electrical connectors 202 on the neurostimulator IPG-facing input 204 of the adapter matrix 200 as well. For example, the microprobes 212 may be of a size and spacing such that a few, such as three, microprobes, contact and are effective to and a signal to an electrical connector 226 of the connector array 224. In another example, the microprobes 212 may be of a size and spacing such that a multiplicity of microprobes, contact and are effective to and a signal to an electrical connector 226 of the connector array 224. In the example, the microprobes 212 are generally regularly spaced apart along the entire microprobe array. The microprobes 212 may be of the order tens of microns or hundreds of microns in size. The configuration of the microprobes 212 may be 30 degrees to 45 degrees from a plane of the adapter matrix 200 to protect the microprobes from fracture when the nonstandard implantable medical lead 220 is inserted into the tissue-facing input 208. In some embodiments, the microprobes 212 may be defaulted to a wider position to enable the insertion of the non-standard lead 220 after which point a mechanical translation or mechanical rotational element could depress the microprobes towards the non-standard lead, 220, in order to make electrical connections.

In the illustrated example, the microprobes 212 can be generally regularly spaced along the tissue-facing input 208. For example, the microprobes are sized such that multiple microprobes 212 contact one connector 226 of the array 224 of the non-standard electrical lead 220 and a microprobe, such as one or more microprobes, contacts the proximal end 222 of the non-standard electrical lead 220 between the connectors 226 of the array 224, such as a nonconductive portion of the proximal end 222. The microprobes 212 are sized and spaced together so as effectively conduct a signal with a connector 226 of the array 224 of the non-standard electrical lead 220. A connector 226 of the array of 224 of the nonstandard electrical lead 220 interfaces, such as mechanically and electrically connects with, a plurality of microprobes and another microprobe mechanically contacts a non-conductive portion of the proximal end 222 of the lead 220 beside a connector, such as between two connectors of array 224. In one example, a first group of a plurality of microprobes interfaces with a connector 224 of the array 226 and a second group of at least one microprobe mechanically contacts a non-conductive portion of the proximal end 222.

The microprobes 212 are spaced along a length of the tissue-facing input 208 such that an entire connector array 224 of the non-standard electrical lead will contact microprobes. As such, the length of array the microprobes of the tissue-facing input can be selected to be longer than at least a significant set of electrical leads that may be implemented with the Illustrated microprobes 212 of the second set of electrical connections 206 include microprobes "a"-"e". In the example, microprobes "a"-"e" mechanically contact the nonstandard implantable medical lead 220 at the proximal end 222 within the tissue-facing input 208. In the example, a first set of microprobes "b", "c", "d", "e" contact electrical connector 226, and microprobe "a" does not contact an electrical connector 226 of connector array 224. Instead, microprobe "a" contacts an insulated portion of the proximal end 222. Microprobes "b"-"e" are in electrical communication with the electrical connector 226 and microprobe "a" is not in electrical communication with the electrical connector 226. In programming the switch matrix 210, microprobes "b"-"e" are selectively coupled to a corresponding electrical connector in the first set of electrical connectors 202, and, in one example, microprobe "a" is not coupled to an electrical connector of the first set of electrical connectors 202.

Further, if a second set of microprobes is in electrical communication with a different electrical connector of connector array 224, the second set of microprobes are selectively coupled to a corresponding electrical connection in the first set of electrical connectors 202, which may be different that the electrical connection of the first set of electrical connectors 202 that is selectively coupled to microprobes "b"-"e" of the first set of microprobes.

In one example, microprobe "a" is an inactive microprobe or inactive conductor whereas microprobes "b"-"e" are active microprobes or active conductors. By determining which active microprobes should correspond with electrical contacts of the stimulation circuitry, appropriate connections can be made with the switch matrix 210 to selectively couple the active microprobes to the first set of electrical connections 202. For example, a stimulation signal $S_0$ from the stimulation circuitry of implantable medical device 30 is provided via an extension lead to a connection $I_a$ of the first set of electrical connections 202, and that stimulation signal is to be provided to connector $L_b$ of the nonstandard electrical lead 220. The active microprobes of microprobes 212 that are in electrical communication with connector $L_b$ can be determined. The active microprobes in electrical communication with connector $L_b$ are to be selectively coupled via switch matrix 210 to connection $I_a$ of the first set of electrical connections 202. This process can be repeated for each of connectors $L_a$-$L_n$ of connector array 222 to selectively electrically couple to a corresponding connection $I_a$-$I_n$ of the first set of electrical connections 202

In some embodiments, the system may employ an algorithm for checking the impedance values between each of the microprobes in the array 206. This could automatically determine which probes are shorted together, e.g. "b"-"e" in FIG. 5, and which are open (a in FIG. 5). This could then result in configuration of the switch matrix so that the system recognizes which probes should be electrically connected to the implantable medical device. In one example, if multiple probes are connected to the same electrode on the non-standard side (222), the switch matrix 210 may connect one of the center probes, such as microprobes "c" or "d", to the non-standard electrode 226. This control logic could reside in the implantable medical device or in the switch matrix or in an external system in communication with the implanted system elements.

Although the present disclosure has been described with reference to preferred embodiments, workers skilled in the art will recognize that changes can be made in form and detail without departing from the spirit and scope of the present disclosure.

What is claimed is:

1. An implantable electrical stimulation medical system comprising:
   an implantable medical device having electrical circuitry configured to deliver electrical stimulation;
   an implantable medical lead having a plurality of connectors that are at least one of sized or spaced so that the implantable medical lead is incompatible to be directly coupled to connectors within the implantable medical device; and
   an adapter matrix configured to electrically interface with the electrical circuitry and the implantable medical lead to provide electrical stimulation from the implantable medical device to the implantable medical lead,
   wherein the adapter matrix comprises:
      a neurostimulator implantable pulse generator (IPG)-facing input having a first set of electrical connections that face the implantable medical device and a tissue-facing input having a second set of electrical connections, the second set of electrical connections includes a plurality of conductive microprobes, the first set of electrical connections selectively electrically coupleable to the second set of electrical connections,
wherein the first set of electrical connections are configured to electrically interface with the electrical circuitry, and wherein the second set of electrical connections having the plurality of conductive microprobes are configured to electrically interface with the implantable medical lead to deliver electrical stimulation from the implantable medical device to the implantable medical lead,
wherein two or more conductive microprobes of the plurality of conductive microprobes are configured to electrically interface with a single connector of the plurality of connectors of the implantable medical lead,
wherein the adapter matrix includes a first switch and a second switch,
wherein a first electrical connection of the first set of electrical connections is coupled to a first side of the first switch and a first side of the second switch,
wherein a first conductive microprobe of the two or more conductive microprobes is coupled to a second side of the first switch, and
wherein a second conductive microprobe of the two or more conductive microprobes is coupled to a second side of the second switch,
wherein the system further comprises control logic circuitry configured to determine that the first conductive microprobe and the second conductive microprobe are coupled to the single connector based on an impedance between the first conductive microprobe and the second conductive microprobe indicating that the first conductive microprobe and the second conductive microprobe are shorted together.

2. The implantable electrical stimulation medical system of claim 1, wherein the adapter matrix is configured to be electrically coupled to the implantable medical device via an extension lead through the IPG-facing input.

3. The implantable electrical stimulation medical system of claim 2, wherein the implantable medical lead is a first implantable medical lead, and wherein the extension lead is a second implantable medical lead having a plurality of connectors that are compatible to be directly coupled to the connectors within the implantable medical device.

4. The implantable electrical stimulation medical system of claim 1, wherein the adapter matrix is configured to be coupled directly to the electrical circuitry.

5. The implantable electrical stimulation medical system of claim 4, wherein the implantable medical device includes a container to enclose the electrical circuitry, and the adapter matrix is disposed within the container.

6. The implantable electrical stimulation medical system of claim 1, wherein the adapter matrix includes a switch matrix selectively electrically coupling the first set of connections to the second set of electrical connections, and wherein the programmable switch matrix includes the first switch and the second switch.

7. The implantable electrical stimulation medical system of claim 1, wherein the adapter matrix includes communication circuitry.

8. The implantable electrical stimulation medical system of claim 1, wherein the adapter matrix includes an affixed extension lead configured to be electrically coupled to the implantable medical device.

9. An adapter matrix for an implantable electrical stimulation system having an implantable medical device having electrical circuitry configured to deliver electrical stimulation to an implantable medical lead, the implantable medical lead having a plurality of connectors that are at least one of sized or spaced so that the implantable medical lead is incompatible to be directly coupled to connectors within the implantable medical device,
wherein the adapter matrix comprises:
a neurostimulator implantable pulse generator (IPG)-facing input having a first set of electrical connections that face the implantable medical device and a tissue-facing input having a second set of electrical connections, the second set of electrical connections includes a plurality of conductive microprobes, the first set of electrical connections selectively electrically coupleable to the second set of electrical connections;
wherein the first set of electrical connections are configured to electrically interface with the electrical circuitry, and wherein the second set of electrical connections having the plurality of conductive microprobes are configured to electrically interface with the implantable medical lead to deliver the electrical stimulation from the implantable medical device to the implantable medical lead,
wherein two or more conductive microprobes of the plurality of conductive microprobes are configured to electrically interface with a single connector of the plurality of connectors of the implantable medical lead,
wherein the adapter matrix includes a first switch and a second switch,
wherein a first electrical connection of the first set of electrical connections is coupled to a first side of the first switch and a first side of the second switch,
wherein a first conductive microprobe of the two or more conductive microprobes is coupled to a second side of the first switch, and
wherein a second conductive microprobe of the two or more conductive microprobes is coupled to a second side of the second switch,
wherein the adapter matrix is configured to enable control logic circuitry to determine that the first conductive microprobe and the second conductive microprobe are coupled to the single connector based on an impedance between the first conductive microprobe and the second conductive microprobe indicating that the first conductive microprobe and the second conductive microprobe are shorted together.

10. The adapter matrix of claim 9, wherein the first set of electrical connections are selectively electrically coupleable to the second set of electrical connections via a programable switch matrix, and wherein the programmable switch matrix includes the first switch and the second switch.

11. The adapter matrix of claim 10, wherein the switch matrix includes an integrated circuit.

12. The adapter matrix of claim 10, wherein the switch matrix, via the first switch and the second switch, is programmable to selectively couple the first electrical connection of the first set of electrical connections to the first conductive microprobe and the second conductive microprobe of the two or more conductive microprobes.

13. The adapter matrix of claim 10, further comprising a power source operably coupled to the switch matrix.

14. The adapter matrix of claim 9, wherein the tissue facing input is configured to receive a proximal end of the implantable medical lead, the proximal end having an array of spaced-apart electrical connectors separated by a nonconductive portion,
   wherein a spaced-apart electrical connectors of the spaced-apart electrical connectors is the single connector,
   wherein the first conductive microprobe and the second conductive microprobe of the two or more microprobes of the plurality of conductive microprobes are configured to be in contact with the spaced-apart electrical connector of the array of spaced-apart electrical connectors via the first electrical connection of the first set of electrical connections and another conductive microprobe of the plurality
of conductive microprobes is configured to be in contact with the nonconductive portion.

15. The adapter matrix of claim 9, wherein the implantable medical lead is a first implantable medical lead, and wherein the IPG-facing input is configured to receive a second implantable medical lead having a plurality of connectors that are compatible to be directly coupled to the connectors within the implantable medical device.

16. The adapter matrix of claim 9, wherein the IPG-facing input further includes an affixed extension lead configured to be electrically coupled to the implantable medical device.

* * * * *